(12) United States Patent
Nigam et al.

(10) Patent No.: US 8,190,247 B2
(45) Date of Patent: May 29, 2012

(54) DEVICE, METHOD AND COMPUTER-READABLE STORAGE MEDIUM FOR DETECTING AND CLASSIFYING OF CARDIAC EVENTS

(75) Inventors: Indra B. Nigam, Tigard, OR (US); Dirk Muessig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 476 days.

(21) Appl. No.: 12/579,305

(22) Filed: Oct. 14, 2009

(65) Prior Publication Data
US 2010/0099996 A1 Apr. 22, 2010

Related U.S. Application Data

(63) Continuation-in-part of application No. 12/254,728, filed on Oct. 20, 2008, now Pat. No. 8,024,031.

(51) Int. Cl.
*A61B 5/04* (2006.01)
(52) U.S. Cl. .............. 600/515; 600/518; 607/4
(58) Field of Classification Search ............ 600/515, 600/518; 607/2, 4, 9, 14
See application file for complete search history.

(56) References Cited

U.S. PATENT DOCUMENTS

| 4,880,005 | A | 11/1989 | Pless |
| 5,462,060 | A | 10/1995 | Jacobson |
| 6,671,548 | B1 | 12/2003 | Mouchawar |
| 7,970,463 | B2 * | 6/2011 | Perschbacher et al. ........... 607/4 |

FOREIGN PATENT DOCUMENTS
WO 02/056961 7/2002

OTHER PUBLICATIONS

European Search Report for Application No. 09172863.4, dated Jan. 26, 2010, 8 pages.

* cited by examiner

*Primary Examiner* — Brian T Gedeon
(74) *Attorney, Agent, or Firm* — ARC IP Law, PC; Joseph J. Mayo

(57) ABSTRACT

Method for detecting cardiac events, e.g., Atrial Fibrillation (AF) or termination of AF. Based on analysis of the instability observed in heart rate, caused by irregular conduction from the atrium during AF. Change in heart interval is monitored on beat-to-beat basis to recognize instability that indicates presence of AF or Atrial Flutter. A packet of a number of consecutive intervals is evaluated, whether the length of an interval is stable compared with the length of the preceding interval, or whether the length of the subsequent interval has changed. After detection of an instability, instability counter is incremented. The result of the stability test for a packet of intervals is represented by the value of the instability counter. Depending upon whether or not an AF already declared, (indicated by AF status flag), different "X-out-of-Y" criterion are applied. AF status flag set/cleared when declaring AF/termination of AF.

14 Claims, 2 Drawing Sheets

DEVICE, METHOD AND COMPUTER-READABLE STORAGE MEDIUM FOR DETECTING AND CLASSIFYING OF CARDIAC EVENTS

This application is a continuation in part of U.S. patent application Ser. No. 12/254,728, filed 20 Oct. 2008 now U.S. Pat. No. 8,024,031 the specification of which is hereby incorporated herein by reference.

BACKGROUND OF THE INVENTION

1. Field of the Invention

Embodiments of the invention generally relate to implantable cardiac devices, including monitoring devices, pacemakers, defibrillators and cardioverters, which monitor, detect and classify cardiac events, for example atrial tachyarrhythmias. More particularly, embodiments of the invention relate to a method and device for detecting Atrial Fibrillation or Atrial Flutter by evaluating ventricular signals. Further, embodiments of the invention relate to methods for monitoring atrial events for use in implantable devices without atrial electrodes.

2. Description of the Related Art

There are previously proposed methods for detecting atrial tachyarrhythmias and a determination of their being stable or unstable. However, an otherwise simple task is complicated by the fact that a multi-chamber pacemaker or ICD may not "see" all of the atrial complexes due to some of these falling in cross-chamber blanking periods, such as post-ventricular-pace blanking and far-field blanking periods.

It is known from the prior art to use a so called "X-out-of-Y" criterion to detect an ongoing atrial tachyarrhythmia. The U.S. Pat. No. 6,671,548 B1 for example describes use of such a "X-out-of-Y" criterion. This criterion declares detection of an atrial tachyarrhythmia when X number of intervals among most recent Y number of atrial intervals are found to be shorter than an interval limit corresponding to the tachyarrhythmia rate limit. The numbers X, Y and the tachyarrhythmia rate limit may be user defined, e.g., pre-defined or may be programmable. As is clear, the "X-out-of-Y" criterion accommodates for undersensing of some of the atrial events.

BRIEF SUMMARY OF THE INVENTION

It is an objective of embodiments of the invention to provide a device, for example an implantable cardiac device, such as a monitoring device, especially a monitoring device without atrial electrodes, but also such as a pacemaker, a defibrillator or a cardioverter, for evaluating cardiac events, such as ventricular signals, for detecting atrial arrhythmia such as Atrial Fibrillation or Atrial Flutter. The device comprises control and storage means and is arranged for executing a method for classifying atrial tachyarrhythmia, the method comprising the following steps:

One aspect of the invention is to provide a method for detecting cardiac events, such as for example Atrial Fibrillation (AF) or termination of the AF. The method is based on the analysis of the instability observed in the heart rate, known to be caused by irregular conduction from the atrium during an episode of AF. Change in the heart interval is monitored on a beat-to-beat basis in an attempt to recognize the instability that indicates presence of an Atrial Fibrillation or Atrial Flutter. According to a preferred embodiment of the invention, the heart intervals are ventricular intervals. The number of false indications is reduced by incorporating features for recognizing Premature Ventricular Contractions and beat detections associated with noise. All clinically significant episodes can be detected. The number of false detections is kept at minimum and below a limit that is tolerated by the attending physician. The design is suitable for incorporation in an implantable device. This is a method, suitable for an implantable device, with high sensitivity and positive predictive values (very few false AF detections).

According to this inventive method discrete packets of consecutive heart intervals are analyzed. The size n of the packet is predetermined. The packet can comprise for example 8, 16, 24, 32 or another number of intervals.

For at least a part of the consecutive intervals of the packet, differences between consecutive intervals in the packet are evaluated. However, preferably for each packet containing n intervals, n−1 such evaluations are made. The evaluation comprises comparison of the differences with a pre-determined stability limit. In a preferred embodiment the stability limit is calculated as a settable percentage of the average value of the intervals of the interval packet. The value can be programmed for example to 6.25%, 12.5% or 18.75%. In a preferred embodiment both, differences and stability limit are weighted. As weights any values may be used, preferably values of 1 or 2 may be used.

The percentage value for the stability limit for different cardiac events can be equal, or it can be chosen independently for each event. For example, the percentage value for the stability limit for AF detection may be equal to that of detection of termination of the AF, or it may be chosen independently for both, AF detection and termination detection.

According to the inventive method an instability counter is calculated depending from the result of the comparison of the differences with the pre-determined stability limit. According to a preferred embodiment of the invention, the instability counter is incremented for each evaluation that indicates instability as per the following test:

the absolute value of the difference between a current interval of the packet and the preceding interval of the packet is greater than the stability limit, and the absolute value of the difference between twice the current interval of the packet and the preceding interval of the packet is greater than twice the stability limit, and the absolute value of the difference between the current interval of the packet and twice the preceding interval of the packet is greater than twice the stability limit.

Written in pseudo-code, the criterion reads:

Absolute [Current Interval−Preceding Interval]>Stability Limit; AND

Absolute [2*Current Interval−Preceding Interval]> 2*Stability Limit; AND

Absolute [Current Interval−2*Preceding Interval]> 2*Stability Limit.

According to embodiments of the invention, a pre-determined event compare limit is used to confirm whether or not a packet analysis indicates presence of the cardiac event to be detected. To determine whether the cardiac event in the interval packet is indicated, the value of the instability counter is compared with the event compare count limit. In a preferred embodiment, a presence of AF is indicated if the instability counter is equal to or greater than the said AF compare count limit. In another preferred embodiment, an absence of AF is indicated if the instability counter is equal to or less than the said termination compare count limit. If the packet contains n intervals, the event compare count limit can be programmed in the range 1 to n−1, i.e. it depends from the chosen packet size.

According to embodiments of the invention, a predetermined event packet hysteresis is used. The cardiac event is declared, if presence of the cardiac event is indicated in a pre-determined number of consecutive interval packets. For example, Atrial Fibrillation is declared, if presence of Atrial Fibrillation is indicated for a pre-determined number of consecutively analyzed interval packets. Analogously, termination of Atrial Fibrillation is declared, if absence of Atrial Fibrillation is indicated for a pre-determined number of consecutively analyzed interval packets. The event packet hysteresis can be programmed to 1, 2, 3 or 4, and depends preferably from the chosen packet size.

A further object of the invention is providing noise options and options for Premature Ventricular Contraction (PVC). It is proposed to execute for a heart beat which is associated with noise or for a heart beat which is recognized as a Premature Ventricular Contraction at least one of the following steps:
  the current heart interval and the following heart interval are excluded from analysis; and
  a new interval packet is created starting from the heart beat that follows the next heart beat.

In a preferred embodiment for each case, noise and PVC, there are four options proposed:
  Noise Options:
1. For a heart beat associated with noise, the current and the following heart intervals are excluded from the analysis.
2. For a heart beat associated with noise, the instability counter is decremented by one and the current and the following heart intervals are excluded from the analysis. If the instability counter becomes zero, a new packet is created starting from the heart beat that follows the next heart beat. This Option can be used only when attempting to detect AF.
3. For a heart beat associated with noise, the instability counter is incremented by one and the current and the following heart intervals are excluded from the analysis. If the instability counter becomes equal to the termination compare count limit, it is cleared and a new packet is created starting from the heart beat that follows the next heart beat. This Option can be used only when attempting to detect termination of AF.
4. For a heart beat associated with noise, the instability counter is cleared and a new packet is created starting from the heart beat that follows the next heart beat.
  PVC Options:
1. For a heart beat recognized as a Premature Ventricular Contraction (PVC), the current and the following heart intervals are excluded from the analysis.
2. For a heart beat recognized as a PVC, the instability counter is decremented by one and the current and the following heart intervals are excluded from the analysis. If the instability counter becomes zero, a new packet is created starting from the heart beat that follows the next heart beat. This Option can be used only when attempting to detect AF.
3. For a heart beat recognized as a PVC, the instability counter is incremented by one and the current and the following heart intervals are excluded from the analysis. If the instability counter becomes equal to the termination compare count limit, it is cleared and a new packet is created starting from the heart beat that follows the next heart beat. This Option can be used only when attempting to detect termination of AF.
4. For a heart beat recognized as a PVC, the instability counter is cleared and the current and a new packet is created starting from the heart beat that follows the next heart beat.

In summary, the inventive method is based on evaluation of the variability of ventricular intervals during occurrence of atrial arrhythmia. According to a first step of the inventive method, a packet of a number of consecutive intervals is evaluated, whether the length of an interval is stable compared with the length of the preceding interval, or whether the length of the subsequent interval has changed. After detection of an instability, the instability counter is incremented.

The result of the stability test for a packet of intervals is represented by the value of the instability counter. Depending upon whether or not an Atrial Fibrillation (AF) has been declared, which is indicated by an AF status flag, different "X-out-of-Y" criterion are applied. The AF status flag is set or cleared when declaring an AF or when declaring termination of an AF respectively. After this, the instability counter is reset, and the next packet of intervals is evaluated.

It is a further objective of embodiments of the invention to provide a device for detecting cardiac events comprising control and storage means, the device being arranged for executing a method for detecting cardiac events, the method comprising an analysis with the steps of:
  for an interval packet comprising a number of consecutive heart intervals calculating for at least a part of the consecutive heart intervals the difference between pairs of consecutive heart intervals;
  comparing the differences with at least one stability limit;
  calculating an instability counter depending from the result of the comparison in the comparing step;
  determining whether the cardiac event in the interval packet is indicated by comparing the value of the instability counter with a settable event compare count limit; and
  declaring the cardiac event if presence of the cardiac event is indicated in a pre-defined number of consecutive interval packets.

According to a preferred embodiment of the invention the implantable device is realized as a pure monitoring device, which does not stimulate the heart. In contrary to the prior art, such an inventive implantable device do not comprise cardiac electrodes. Instead, in a preferred embodiment the inventive implantable device detects respective electrical potential with the help of electrodes provided by the enclosure of the implantable device. According to a preferred embodiment of the invention, the implantable device has an enclosure, which is made from an electrically conductive and biocompatible material like titanium for example. In another preferred embodiment the implantable device is made of a conductive body covered with a non-conductive material. Preferably, the non-conductive enclosure has one or more holes that allow the conductive body to contact the surrounding tissue.

Using such an implantable device, the amplitudes of atrial signals is very low. Therefore, detection and evaluation of atrial signals is difficult. Therefore, in a preferred embodiment of the invention, ventricular signals are evaluated for detecting atrial arrhythmia, such as Atrial Fibrillation or Atrial Flutter, without knowledge of atrial events or atrial intervals. According to a preferred embodiment of the invention, the presence or absence of events such as AF is identified only by evaluating the ventricular intervals.

However, this device may be an implantable cardiac device, such as a pacemaker (especially without atrial electrodes), a defibrillator or a cardioverter.

A further objective of the invention is to provide a computer-readable storage medium storing program code for causing a data processing device to perform a method for detecting cardiac events, the method comprising an analysis with the steps of:

for an interval packet comprising a number of consecutive heart intervals calculating for at least a part of the consecutive heart intervals the difference between pairs of consecutive heart intervals;

comparing the differences with least one stability limit;

calculating an instability counter depending from the result of the comparison in the comparing step;

determining whether the cardiac event in the interval packet is indicated by comparing the value of the instability counter with a settable event compare count limit; and declaring the cardiac event if presence of the cardiac event is indicated in a pre-defined number of consecutive interval packets.

The invention may be implemented in software, hardware or as a mixed-mode solution.

DETAILED DESCRIPTION OF THE INVENTION

Figure 1:
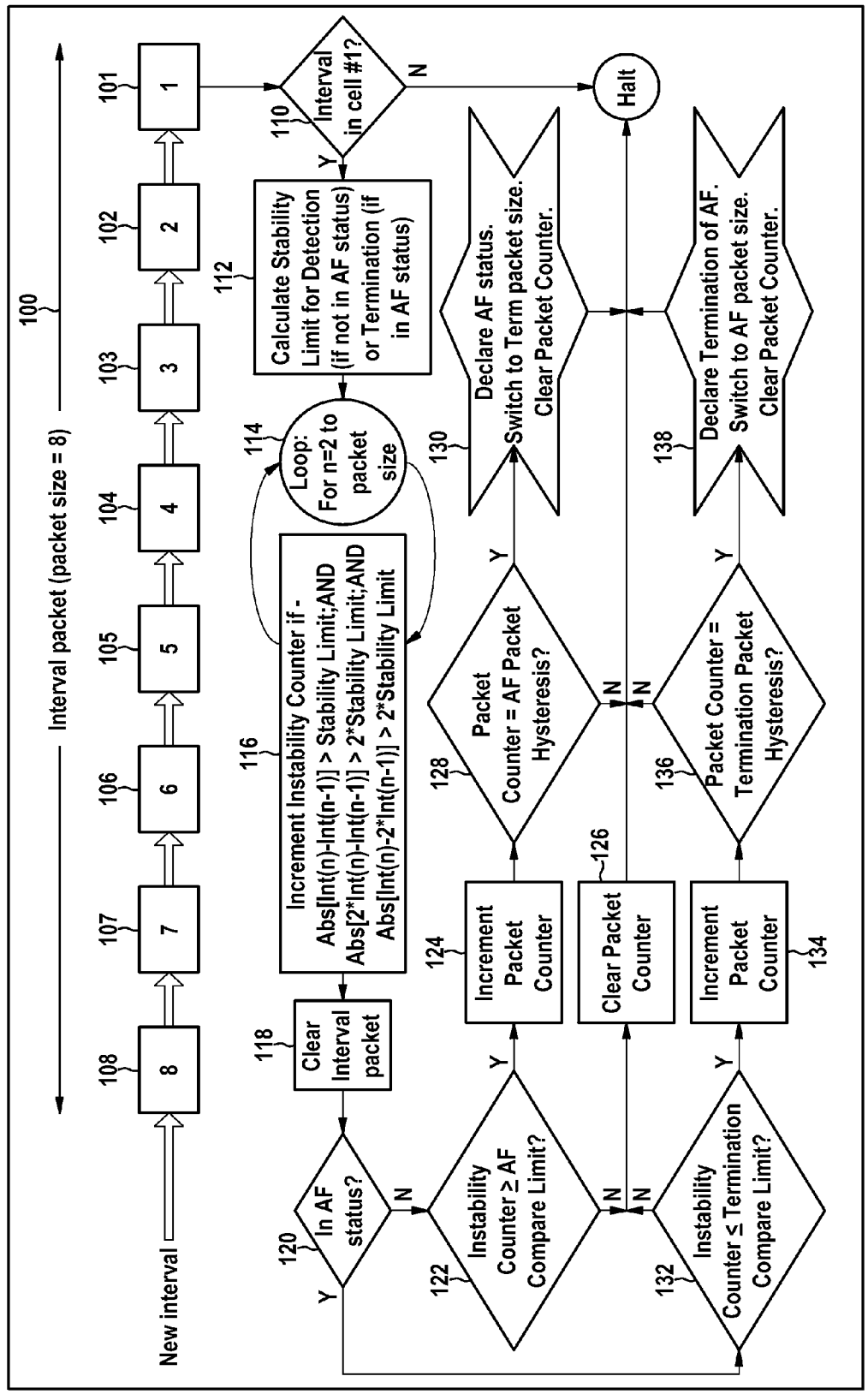
FIG. 1 is a schematic illustration of an embodiment of a method for detecting cardiac events.

FIG. 1 shows an example of a first embodiment of the method for detecting cardiac events. In this special embodiment a packet 100 of eight consecutive intervals is analyzed. The intervals of the packet 100 are stored in cells 101, 102, ..., 108. In step 110 of the analysis it is determined if cell #1 101 contains an interval. If there is detected an interval in cell #1 101 the analysis proceeds with step 112, where the Stability Limit is calculated. In a preferred embodiment the Stability Limit is calculated as a percentage of the of the average value of the intervals in the packet, where for detection of AF another percentage may be used than for detection of other cardiac events such as for detection of termination of AF for example. However, also the same percentage may be used for both, detection of AF and detection of termination of AF.

After determining the Stability Limit in step 112, in a loop 114 the seven differences between consecutive intervals for Int(i) (=2, 3, ..., 8) in the packet are evaluated, and instability is indicated in step 116 if the following criterion is met:

Absolute [Current Interval−Preceding Interval]>
 Stability Limit; AND

Absolute [2*Current Interval−Preceding Interval]>
 2*Stability Limit; AND

Absolute [Current Interval−2*Preceding Interval]>
 2*Stability Limit.

In step 116 the instability counter is incremented by one each time this criterion is met for a pair from the eight consecutive intervals.

Figure 2:
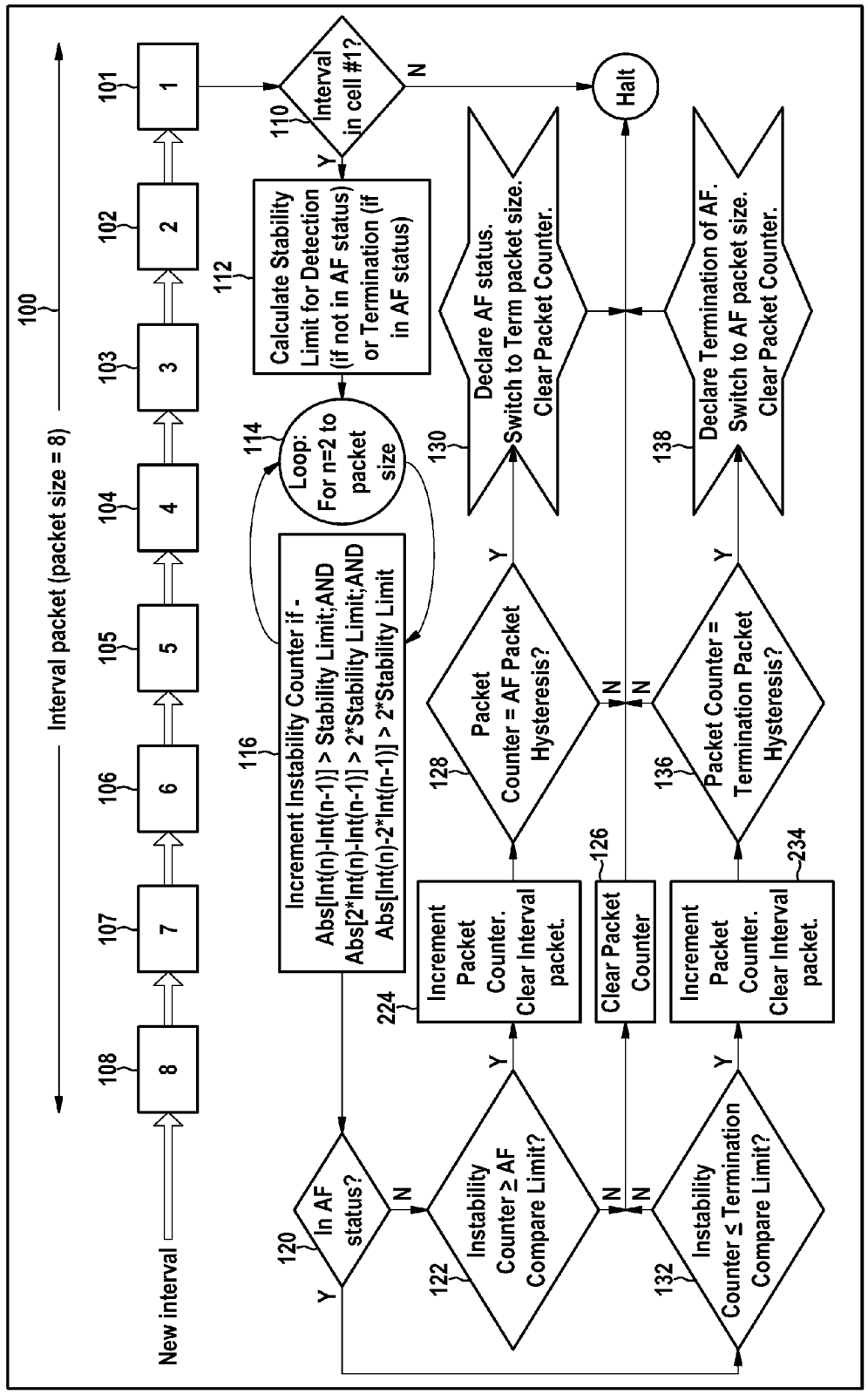
FIG. 2 is a further schematic illustration of an alternative embodiment of a method for detecting cardiac events.

Then, in step 118 of this embodiment, the interval packet 100 is cleared. However, in other embodiments the interval packet 100 may be cleared later, for example in step 224 (see FIG. 2) after the instability counter has been compared with a AF Compare Limit, or in step 234 after the instability counter has been compared with a Termination Compare Limit.

In the next step 120 it is checked whether or not an AF status has been declared or not. When not in AF status, the analysis proceeds with step 122, where the value of the instability counter is compared with a pre-determined AF Compare Limit to decide whether presence of AF is indicated. Presence is indicated in step 122 if the value of the instability counter reaches or exceeds the AF Compare Limit. In this case, a packet counter, which is used in following steps of the analysis, is incremented in step 124.

After the packet counter is incremented in step 124, the packet counter is compared in step 128 with the value of a pre-determined AF Packet Hysteresis. Only if AF presence is indicated for a pre-determined number of consecutively analyzed packets, i.e. the packet counter has reached the value of the AF Packet Hysteresis, AF status is declared in step 130, and the packet counter is cleared.

When already in AF status, which is determined in step 120, the analysis proceeds with step 132, where the value of the instability counter is compared with a pre-determined Termination Compare Limit to decide whether absence of AF is indicated. Absence is indicated in step 132 if the value of the instability counter is equal to or less than the Termination Compare Limit. In this case, the packet counter is incremented in step 134.

After the packet counter is incremented in step 134, the packet counter is compared in step 136 with the value of a pre-determined Termination Packet Hysteresis. Only if AF absence is indicated for a pre-determined number of consecutively analyzed packets, i.e. the packet counter has reached the value of the Termination Packet Hysteresis, termination of the AF is declared in step 138, and the packet counter is cleared.

If it is determined in step 122 that the value of the instability counter is less than the AF Compare Limit, the packet counter is cleared in step 126. Also, if it is determined in step 132 that the value of the instability counter is greater than the Termination Compare Limit, the packet counter is cleared in step 126.

What is claimed is:

1. A method for detecting cardiac events in an implantable cardiac device comprising:
    calculating for at least a portion of consecutive heart intervals selected from an interval packet that comprises a number of the consecutive heart intervals, differences between pairs of the consecutive heart intervals;
    calculating at least one stability limit as a settable percentage of average values of intervals within the interval packet;
    comparing the differences with the at least one stability limit to form a result;
    calculating an instability counter depending on the result of the comparing;
    determining whether a cardiac event in the interval packet is indicated by comparing a value of the instability counter with a settable event compare count limit; and,
    declaring the cardiac event, if presence of the cardiac event is indicated in a pre-defined number of consecutive interval packets.

2. The method according to claim 1, wherein the cardiac event comprises Atrial Fibrillation, and wherein:
    said determining comprises determining whether presence of Atrial Fibrillation in the interval packet is indicated by comparing the value of the instability counter with a pre-defined Atrial Fibrillation compare count limit; and,
    said declaring comprises declaring the Atrial Fibrillation if presence of the Atrial Fibrillation is indicated in the pre-defined number of consecutive interval packets.

3. The method according to claim 2, wherein for a heart beat which is associated with noise or for a heart beat which is recognized as a Premature Ventricular Contraction, one of the following steps is executed:
 a current heart interval and a following heart interval are excluded from analysis; or
 the instability counter is decremented by 1 and the current heart interval and the following heart interval are excluded from analysis, where in case the instability counter becomes 0, a new interval packet is created starting from a heart beat that follows a next heart beat; or
 the instability counter is cleared and the new interval packet is created starting from the heart beat that follows the next heart beat.

4. The method according to claim 1, wherein the cardiac event comprises termination of Atrial Fibrillation, and wherein:
 said determining comprises determining whether absence of Atrial Fibrillation in the interval packet is indicated by comparing the value of the instability counter with a pre-defined termination compare count limit; and,
 said declaring comprises declaring termination of the Atrial Fibrillation if absence of the Atrial Fibrillation is indicated in the pre-defined number of consecutive interval packets.

5. The method according to claim 4, wherein for a heart beat which is associated with noise or for a heart beat which is recognized as a Premature Ventricular Contraction, one of the following steps is executed:
 a current heart interval and a following heart interval are excluded from analysis; or
 the instability counter is incremented by 1 and the current heart interval and the following heart interval are excluded from analysis, where in case the instability counter becomes equal to the pre-defined termination compare count limit, the instability counter is cleared and a new interval packet is created starting from a heart beat that follows a next heart beat; or
 the instability counter is cleared and the new interval packet is created starting from the heart beat that follows the next heart beat.

6. The method according to claim 1, where at least one of the differences and the at least one stability limit is weighted by 1 or 2.

7. The method according to claim 1, wherein said calculating comprises:
 incrementing the instability counter if:
 an absolute value of a difference between a current interval of the interval packet and a preceding interval of the interval packet is greater than the at least one stability limit, and
 an absolute value of a difference between twice the current interval of the interval packet and the preceding interval of the interval packet is greater than twice the at least one stability limit, and
 an absolute value of a difference between the current interval of the interval packet and twice the preceding interval of the interval packet is greater than twice the at least one stability limit.

8. The method according to claim 1, wherein for a heart beat which is associated with noise or for a heart beat which is recognized as a Premature Ventricular Contraction at least one of the following steps is executed:
 a current heart interval and a following heart interval are excluded from analysis; and,
 a new interval packet is created starting from the heart beat that follows a next heart beat.

9. The method according to claim 1, where at least a part of the consecutive heart intervals are ventricular intervals.

10. The method according to claim 9, further comprising detecting atrial arrhythmia from the ventricular intervals.

11. A device for detecting cardiac events wherein said device is configured to:
 calculate for at least a portion of consecutive heart intervals selected from an interval packet that comprises a number of the consecutive heart intervals, differences between pairs of the consecutive heart intervals;
 calculate at least one stability limit as a settable percentage of average values of intervals within the interval packet;
 compare the differences with the at least one stability limit to form a result;
 calculate an instability counter that depends on the result;
 determine whether a cardiac event in the interval packet is indicated through comparison of a value of the instability counter with a settable event compare count limit; and,
 declare the cardiac event, if presence of the cardiac event is indicated in a pre-defined number of consecutive interval packets.

12. The device according to claim 11, wherein the device comprises an enclosure of electrically conductive or of electrically non-conductive material.

13. The device according to claim 12, wherein the electrically non-conductive material covers an electrically conductive body and wherein the electrically non-conductive material comprises one or more holes that allow the electrically conductive body to contact surrounding tissue.

14. A computer-readable storage medium that stores program code configured to cause a data processing device to detect cardiac events, wherein said program code is configured to:
 calculate for at least a portion of consecutive heart intervals selected from an interval packet that comprises a number of the consecutive heart intervals, differences between pairs of the consecutive heart intervals;
 calculate at least one stability limit as a settable percentage of average values of intervals within the interval packet;
 compare the differences with the at least one stability limit to form a result;
 calculate an instability counter that depends on the result;
 determine whether a cardiac event in the interval packet is indicated through comparison of a value of the instability counter with a settable event compare count limit; and, declare the cardiac event, if presence of the cardiac event is indicated in a pre-defined number of consecutive interval packets.

* * * * *